United States Patent
Doty et al.

(10) Patent No.: US 6,821,261 B2
(45) Date of Patent: Nov. 23, 2004

(54) ORTHOPEDIC BRACE HAVING LENGTH-ADJUSTABLE SUPPORTS

(75) Inventors: Del Ray Doty, Carlsbad, CA (US); Alexis Laurand Erwin, Carlsbad, CA (US)

(73) Assignee: DJ Orthopedics, LLC, Vista, CA (US)

( * ) Notice: Subject to any disclaimer, the term of this patent is extended or adjusted under 35 U.S.C. 154(b) by 413 days.

(21) Appl. No.: 10/020,319

(22) Filed: Dec. 11, 2001

(65) Prior Publication Data

US 2002/0072695 A1 Jun. 13, 2002

Related U.S. Application Data

(60) Provisional application No. 60/255,521, filed on Dec. 12, 2000.

(51) Int. Cl.$^7$ .................................................. A61F 5/00
(52) U.S. Cl. .............................. 602/5; 602/16; 602/23; 602/26; 128/882
(58) Field of Search .............................. 602/5, 16, 19, 602/23, 26; 128/846, 869, 882; 606/53, 54

(56) References Cited

U.S. PATENT DOCUMENTS

| | | | |
|---|---|---|---|
| 649,237 A | | 5/1900 | Dyson |
| 1,018,452 A | | 2/1912 | Slaughler |
| 1,780,959 A | | 11/1930 | Wilkes |
| 2,958,325 A | | 11/1960 | Claydon |
| 3,913,570 A | | 10/1975 | Madden et al. |
| D265,248 S | | 6/1982 | Grigorieff |
| 4,381,768 A | | 5/1983 | Erichsen et al. |
| 4,531,515 A | * | 7/1985 | Rolfes .......................... 602/16 |
| 4,632,097 A | | 12/1986 | Brooks |
| D291,596 S | | 8/1987 | Detty |

(List continued on next page.)

FOREIGN PATENT DOCUMENTS

| | | |
|---|---|---|
| DE | 367369 | 1/1923 |
| EP | 1 086 671 A2 | 3/2001 |
| FR | 730670 | 8/1932 |
| FR | 2414325 | 8/1979 |
| GB | 19736 | 11/1902 |
| NL | 12997 | 9/1925 |

OTHER PUBLICATIONS

A copy of United Stated patent application No. 09/608,940, filed on Jun. 30, 2000, entitled *Orthopaedic Brace Having a Range of Motion Hinge with an Adjustable–Length Strut*.

A copy of United State Provisional patent application No. 60/156,342 filed on Sep. 27, 1999 entitled *Orthopaedic Brace Having a Range of Motion Hinge with an Adjustable– Length Strut*.

*Primary Examiner*—Fadi H. Dahbour
(74) *Attorney, Agent, or Firm*—Knobbe, Martens, Olson & Bear, LLP

(57) ABSTRACT

An orthopedic brace having length adjustable supports is provided. The brace comprises upper and lower supports rotatably connected by a hinge. Each of the supports comprises an elongate portion having a channel along part of its length, and a sliding upright that nests within the channel. The upright is incrementally longitudinally translatable within the channel so that the length of the support is adjustable. Flanges are provided along the edges of the channel to prevent lateral separation of the upright from the stationary portion. A spring-biased button protrudes from an upper surface of the channel. The button cooperates with one of a plurality of holes in the upright, providing a positive lock to retain the upright in one of a number of predetermined positions within the channel. The upright is also completely removable from the channel. Removal of the upright from the channel shortens the brace. Straps cooperate with brackets on the supports and/or uprights to secure the brace to a patient's leg.

16 Claims, 13 Drawing Sheets

U.S. PATENT DOCUMENTS

| | | |
|---|---|---|
| 4,768,500 A | 9/1988 | Mason et al. |
| 5,052,379 A | 10/1991 | Airy et al. |
| 5,244,455 A | 9/1993 | Swicegood et al. |
| 5,360,394 A | 11/1994 | Christensen |
| 5,437,619 A | 8/1995 | Malewicz et al. |
| 5,571,078 A | 11/1996 | Malewicz |
| 5,632,725 A | 5/1997 | Silver et al. |
| 5,645,524 A | 7/1997 | Doyle |
| 5,653,680 A * | 8/1997 | Cruz .......................... 602/16 |
| 5,658,241 A * | 8/1997 | Deharde et al. ............... 602/5 |
| 5,669,873 A | 9/1997 | Towsley |
| 5,885,235 A | 3/1999 | Opahle et al. |

* cited by examiner

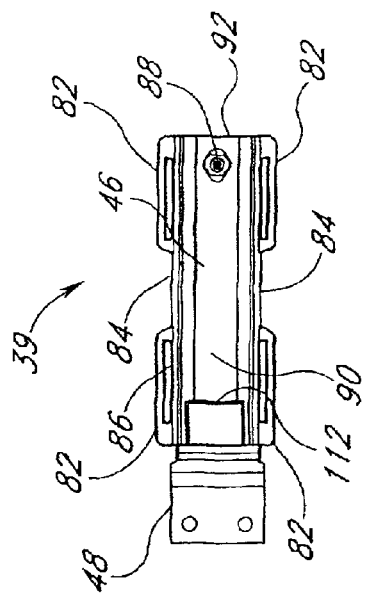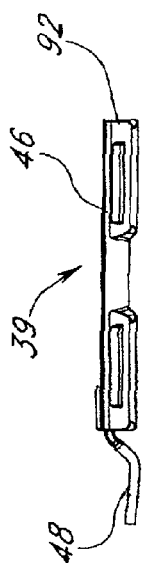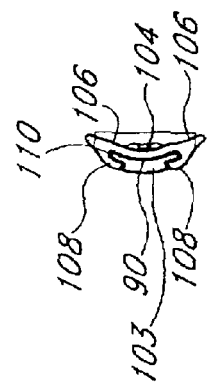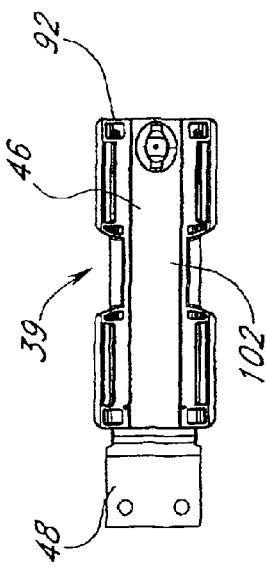

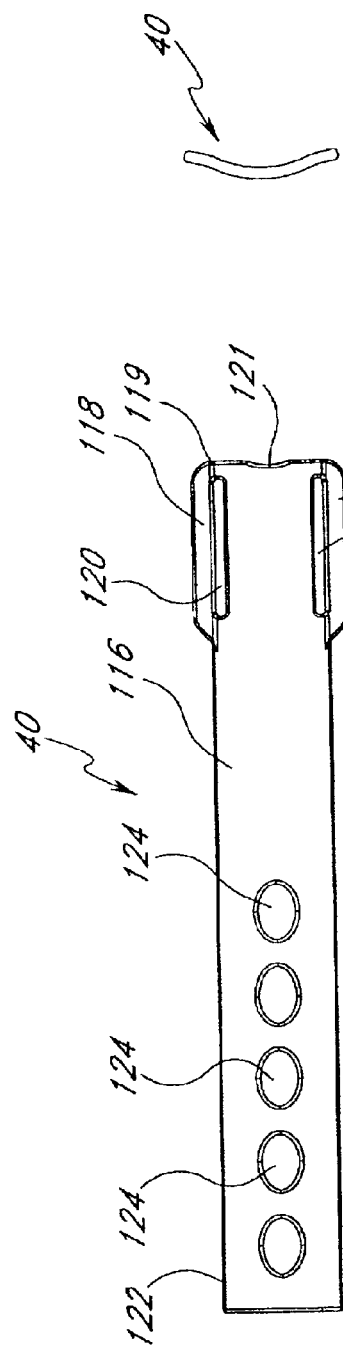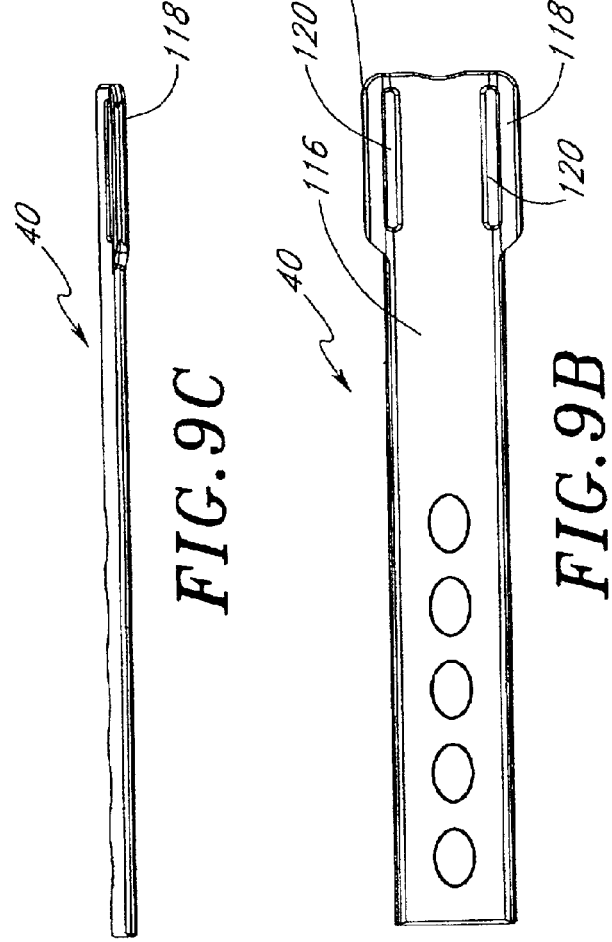

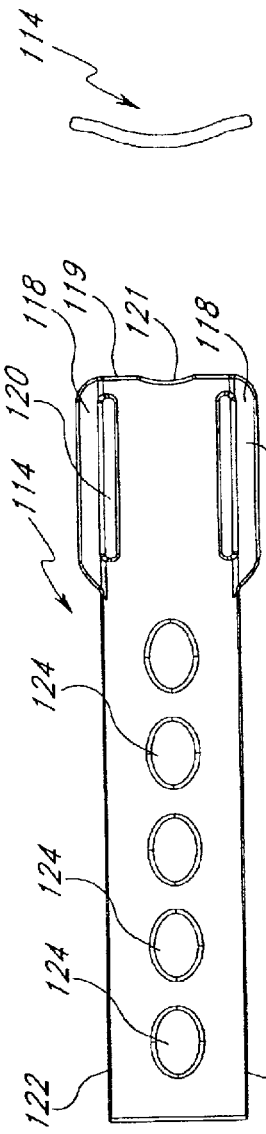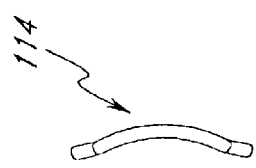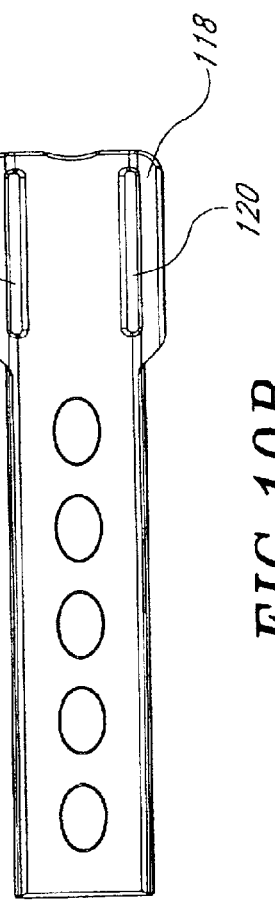
FIG.10D
FIG.10A
FIG.10C
FIG.10B
FIG.10E

ORTHOPEDIC BRACE HAVING LENGTH-ADJUSTABLE SUPPORTS

RELATED APPLICATION

This application claims priority to provisional application Ser. No. 60/255,521, filed on Dec. 12, 2000.

BACKGROUND OF THE INVENTION

1. Field of the Invention

The present invention relates to orthopedic braces and, more particularly, to orthopedic braces having length adjustment capability.

2. Description of the Related Art

Orthopedic braces are commonly employed after surgery or for treatment of injury to a joint. Such braces generally serve to stabilize the joint. In certain cases orthopedic braces limit joint flexion and/or extension in a controllable and adjustable manner to prevent re-injury of the joint and to promote rehabilitation.

Some prior art orthopedic braces include length-adjustable support members. However, these braces typically comprise sidebar components that are merely sandwiched together. This configuration makes them susceptible to prying forces that tend to separate the components.

In addition, some prior art braces use threaded fasteners to connect the sidebar components. Adjusting these braces requires a screwdriver or turning a manual thumbscrew, both of which are inconvenient and time consuming. Such braces are also typically prone to failure due to stripped fastener threads. Other braces rely upon friction, as from tightening a lead screw, to hold the components of the brace in the desired position. These braces, however, do not provide a positive lock, and are thus prone to disadvantageous slippage.

Some prior art braces use an all-aluminum construction. Machining and forming aluminum, however, is relatively expensive and has certain physical limitations. Aluminum thus limits the range of features and style that may be incorporated into the brace.

SUMMARY OF THE INVENTION

The preferred embodiments of the orthopedic brace have several features, no single one of which is solely responsible for their desirable attributes. Without limiting the scope of this orthopedic brace as expressed by the claims that follow, its more prominent features will now be discussed briefly. However, not all of the following features are necessary to achieve the advantages of the orthopedic brace. Therefore, none of the following features should be viewed as limiting. After considering this discussion, and particularly after reading the section entitled "Detailed Description of the Preferred Embodiments," one will understand how the features of the preferred embodiments provide advantages over prior braces. One such advantage is length adjustability so that the amount of restraint offered by the brace may be altered during a course of treatment and so that one brace may fit differently sized patients. Another advantage is that the brace includes a low profile that prevents the brace from snagging objects as the wearer moves about. The brace may be manufactured from a combination of thermoplastic composite and metal that enables the brace to harness the advantages of both materials. Further, the brace may have a length adjustment mechanism that is recessed to prevent accidental activation.

One preferred embodiment of the orthopedic brace comprises a first support, a second support, and a hinge assembly rotatably connecting the first and second supports. At least one of the first and second supports comprises an outer portion defining a longitudinal channel and a telescoping upright movable in the channel to adjust a length of the support.

In another preferred embodiment, at least one strap is provided to wrap around the brace and a patient's leg to secure the brace to the leg.

In another preferred embodiment, at least one padded cuff is disposed between the patient's leg and the brace to increase patient comfort.

In another preferred embodiment, the upright is removable from the at least one of the first and second supports to shorten the overall length of the brace.

In another preferred embodiment, a plurality of engagement surfaces are provided along a length of the telescoping upright, and the outer portion includes an engagement member selectively engageable with the engagement surfaces to lock the telescoping portion in place in the channel.

In another preferred embodiment, the engagement member is recessed within the upright when the engagement member engages one of the engagement surfaces.

In another preferred embodiment, the engagement member comprises a button disposed within a recess in the channel and biased toward a configuration wherein a portion of the button protrudes from a surface of the channel.

In another preferred embodiment, the button has an oval shape in plan aspect.

In another preferred embodiment, the engagement surfaces comprise holes.

In another preferred embodiment, the holes have an oval shape in plan aspect.

In another preferred embodiment, the first and second supports are curved about an axis that is parallel to a longitudinal axis of the brace.

In another preferred embodiment, a cross-section of the first and second supports includes a first region having a first radius of curvature and a second region having a second radius of curvature longer than the first radius of curvature.

In another preferred embodiment, the first region is located between the second region and a third region having the second radius of curvature.

In another preferred embodiment, the first and second supports further comprise at least a first generally D-shaped ring on a first side and a second generally D-shaped ring on a second side opposite the first side.

In another preferred embodiment, the first and second rings are adjacent the hinge assembly.

In another preferred embodiment, the upright comprises at least a first generally D-shaped ring on a first side and a second generally D-shaped ring on a second side opposite the first side.

In another preferred embodiment, the first and second rings are located at an end of the upright opposite the hinge assembly.

In another preferred embodiment, the hinge assembly comprises flexion-limiting stops.

In another preferred embodiment, the hinge assembly comprises extension-limiting stops.

In another preferred embodiment, the orthopedic brace comprises a first support, a second support, and a hinge assembly rotatably connecting the first and second supports. At least one of the first and second supports comprises a first portion constructed of a thermoplastic composite and a second portion constructed of a metal.

In another preferred embodiment, the first portion comprises an outer portion defining a longitudinal channel.

In another preferred embodiment, the second portion comprises a telescoping upright movable in the channel to adjust the length of the support.

In another preferred embodiment, the first portion is connected to a metal hinge plate.

In another preferred embodiment, the hinge plate is insert molded within the first portion.

In another preferred embodiment, a portion of the hinge plate is bendable about an axis that is perpendicular to an axis of rotation of the hinge assembly.

In another preferred embodiment, the orthopedic brace comprises a first length-adjustable support and a second length-adjustable support. Each support includes a longitudinal channel and a sliding upright within the channel. A hinge assembly rotatably connects the first and second supports. Each sliding upright includes a plurality of through holes, and a floor of each channel includes a spring-biased button. The button is engageable with each hole such that the button positively locks a position of the upright with respect to the channel. The upright is slidable within the channel when the button is depressed.

In another preferred embodiment, each support includes a curvature about a longitudinal axis thereof such that substantially all of a surface of each support that faces a patient's leg contacts the leg.

In another preferred embodiment, each support further comprises a plurality of brackets that are adapted to receive flexible straps for securing the brace to a patient's leg.

BRIEF DESCRIPTION OF THE DRAWINGS

The preferred embodiments of the orthopedic brace, illustrating its features, will now be discussed in detail. These embodiments depict the novel and non-obvious orthopedic brace shown in the accompanying drawings, which are for illustrative purposes only. These drawings include the following figures, in which like numerals indicate like parts:

FIG. 6A is a top plan view of a link bar of a calf portion the brace of FIG. 3;

FIG. 6B is a bottom plan view of the link bar of FIG. 6A;

FIG. 6C is a right-side elevation view of the link bar of FIG. 6A;

FIG. 6D is a front elevation view of the link bar of FIG. 6A;

FIG. 9A is a top plan view of a sliding upright of a calf portion of the brace of FIG. 3;

FIG. 9B is a bottom plan view of the sliding upright of FIG. 9A;

FIG. 9C is a front elevation view of the sliding upright of FIG. 9A;

FIG. 9D is a right-side elevation view of the sliding upright of FIG. 9A;

FIG. 9E is a left-side elevation view of the sliding upright of FIG. 9A;

FIG. 10A is a top plan view of a sliding upright of a thigh portion of the brace of FIG. 3;

FIG. 10B is a bottom plan view of the sliding upright of FIG. 10A;

FIG. 10C is a front elevation view of the sliding upright of FIG. 10A;

FIG. 10D is a right-side elevation view of the sliding upright of FIG. 10A;

FIG. 10E is a left-side elevation view of the sliding upright of FIG. 10A;

DETAILED DESCRIPTION OF THE PREFERRED EMBODIMENTS

Figure 1:
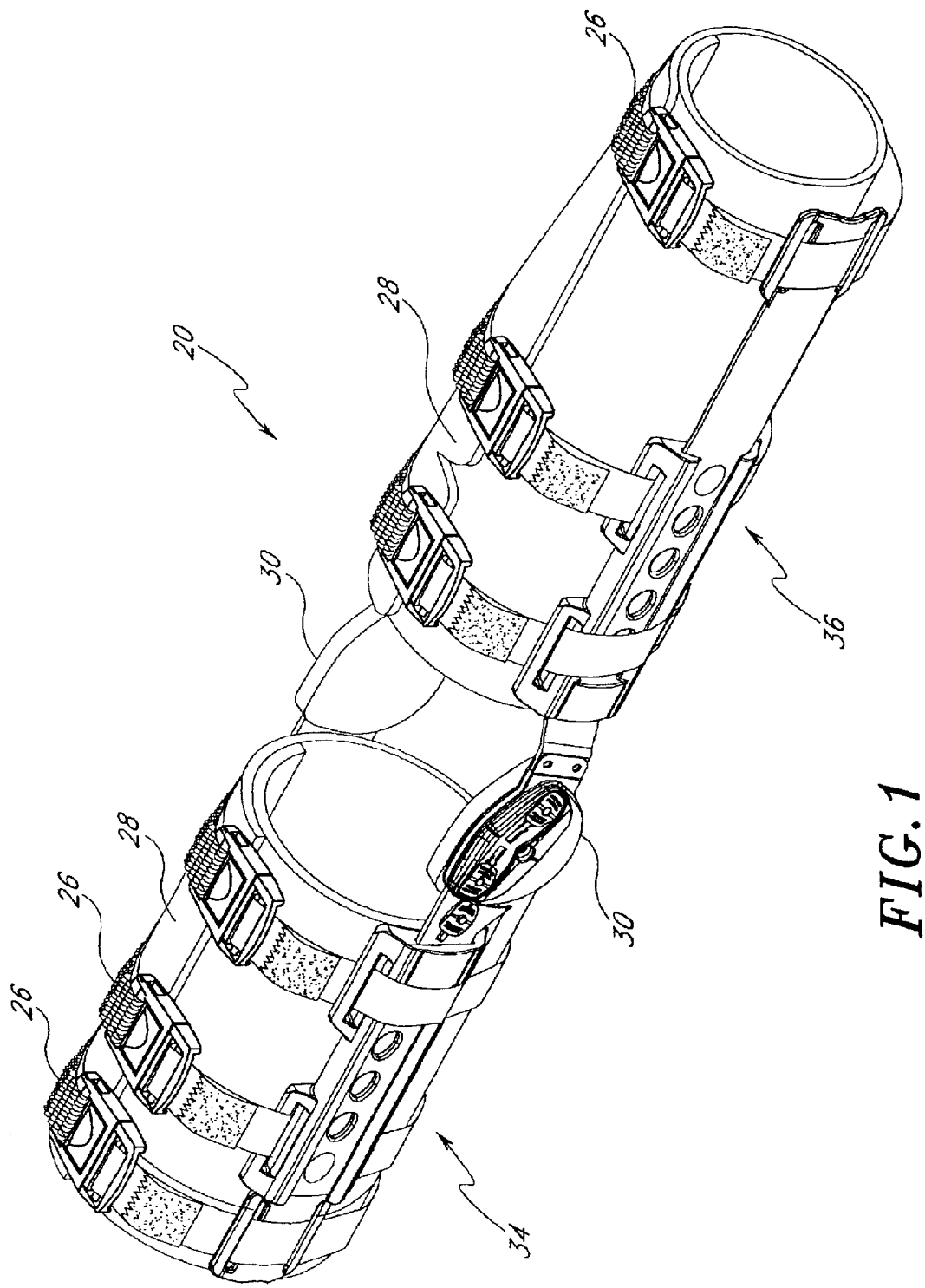
FIG. 1 is a perspective view of a preferred embodiment of the orthopedic brace of the present invention including a right support and a left support, padded cuffs and straps.
Figure 2:
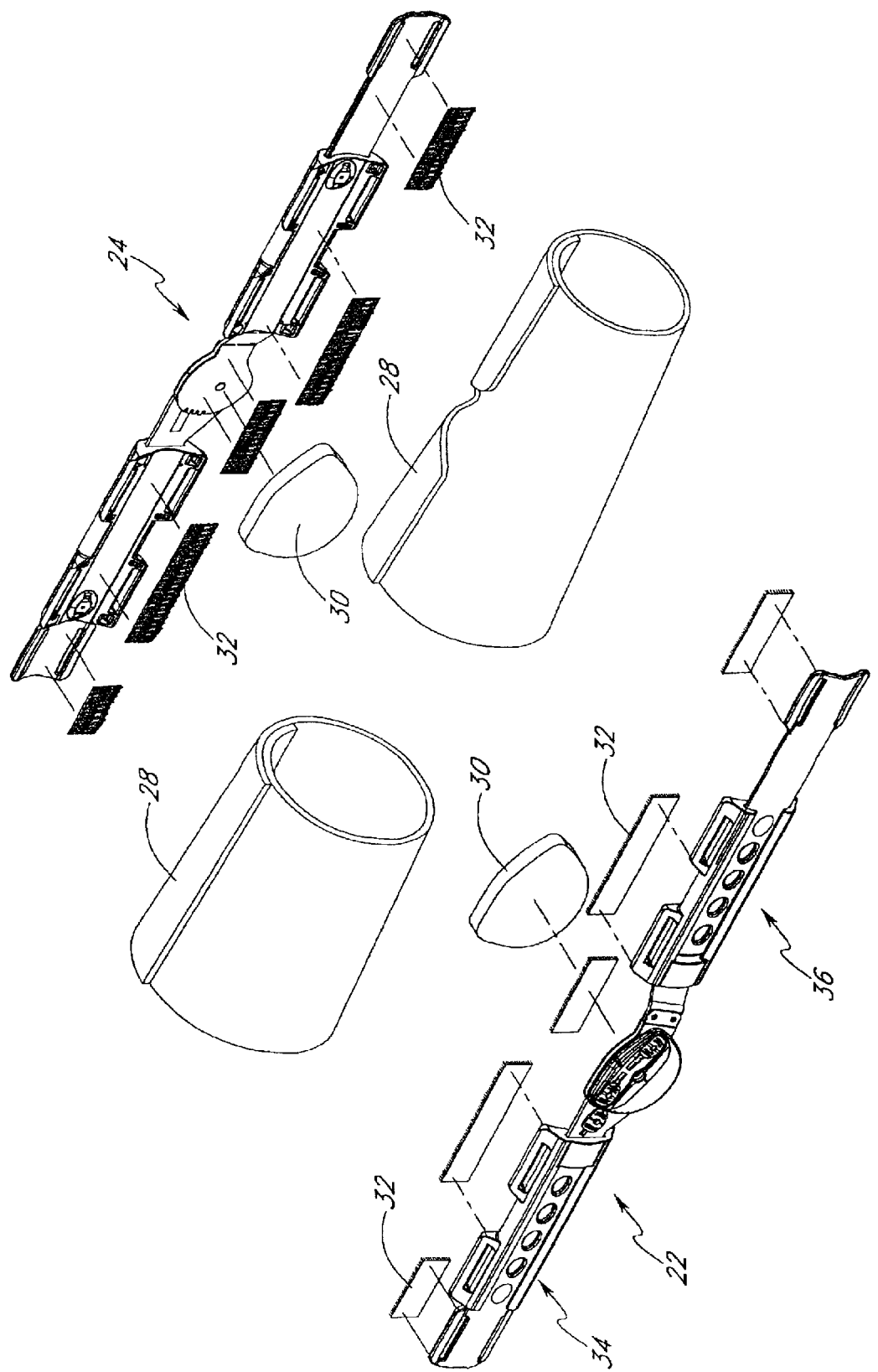
FIG. 2 is a partially exploded perspective view of the brace and padded cuffs of FIG. 1.

FIGS. 1 and 2 illustrate a preferred embodiment of an orthopedic brace 20. In the illustrated embodiment, the orthopedic brace 20 is a knee brace. However, one of skill in the art will appreciate that certain features of the orthopedic brace 20 are applicable to other types of braces as well, such as arm braces, ankle braces, neck braces, and the like.

The embodiment of FIGS. 1 and 2, which is adaptable for use on either the left or the right leg of a patient, comprises a first elongate support 22 for positioning along the right side of the patient's leg, and a second elongate support 24, for positioning along the left side. If desired, only one support may be used for particular applications. In the two support configuration, however, the two supports 22, 24 preferably are mirror images of one another.

The supports 22, 24 are secured to a patient's leg with straps 26 that wrap around the circumference of the leg. In the embodiment illustrated in FIG. 1, six straps 26 are provided. Those of skill in the art will appreciate, however, that fewer or more straps may be used. A plurality of padded cuffs 28 disposed between the supports 22, 24 and the leg provide padding and increase patient comfort. Those of skill in the art will also appreciate that the cuffs 28 merely enhance the wearability of the brace 20, and are not an essential component of the brace 20. A pad 30 may be secured to an inside surface of each support 22, 24 near a midpoint of each support 22, 24. In a preferred embodiment, the cuffs 28 and pads 30 each comprise a layer of foam padding and a layer of a loop portion of a hook-and-loop fastener.

In another preferred embodiment, an inside surface of the cuffs 28 and/or pads 30 comprises a fabric. This surface contacts the patient's leg. Therefore, the fabric is preferably any material that is comfortable for wear against the skin. A preferred material is nylon. Of course, the cuffs need not include a fabric layer on an inside surface. Preferably, however, the cuffs do not irritate the patient's skin.

The loop portion of a hook-and-loop fastener forms an outside surface of the cuffs 28 and pads 30. The outside surface contacts a plurality of inserts 32 which may be disposed between the cuffs 28 and pads 30 and the supports 22, 24. A first face of each insert comprises a hook portion of a hook-and-loop fastener and faces the outside surface of the cuffs 28 and pads 30. A second face, opposite the first face, adhesively attaches the inserts 32 to the inside surfaces of the supports 22, 24. The inserts 32 thus removably secure the supports 22, 24 to the cuffs 28 and pads 30 to prevent migration of the brace 20 relative to the cuffs 28 and pads 30. Rather than including the inserts 32, a variety of other configurations could be used to maintain the relative positions of the brace 20 and cuffs 28. For example, fasteners other than hook-and-loop could be used. Alternatively, the cuffs could be manufactured from neoprene, or another material that has a high coefficient of static friction.

Figure 3:
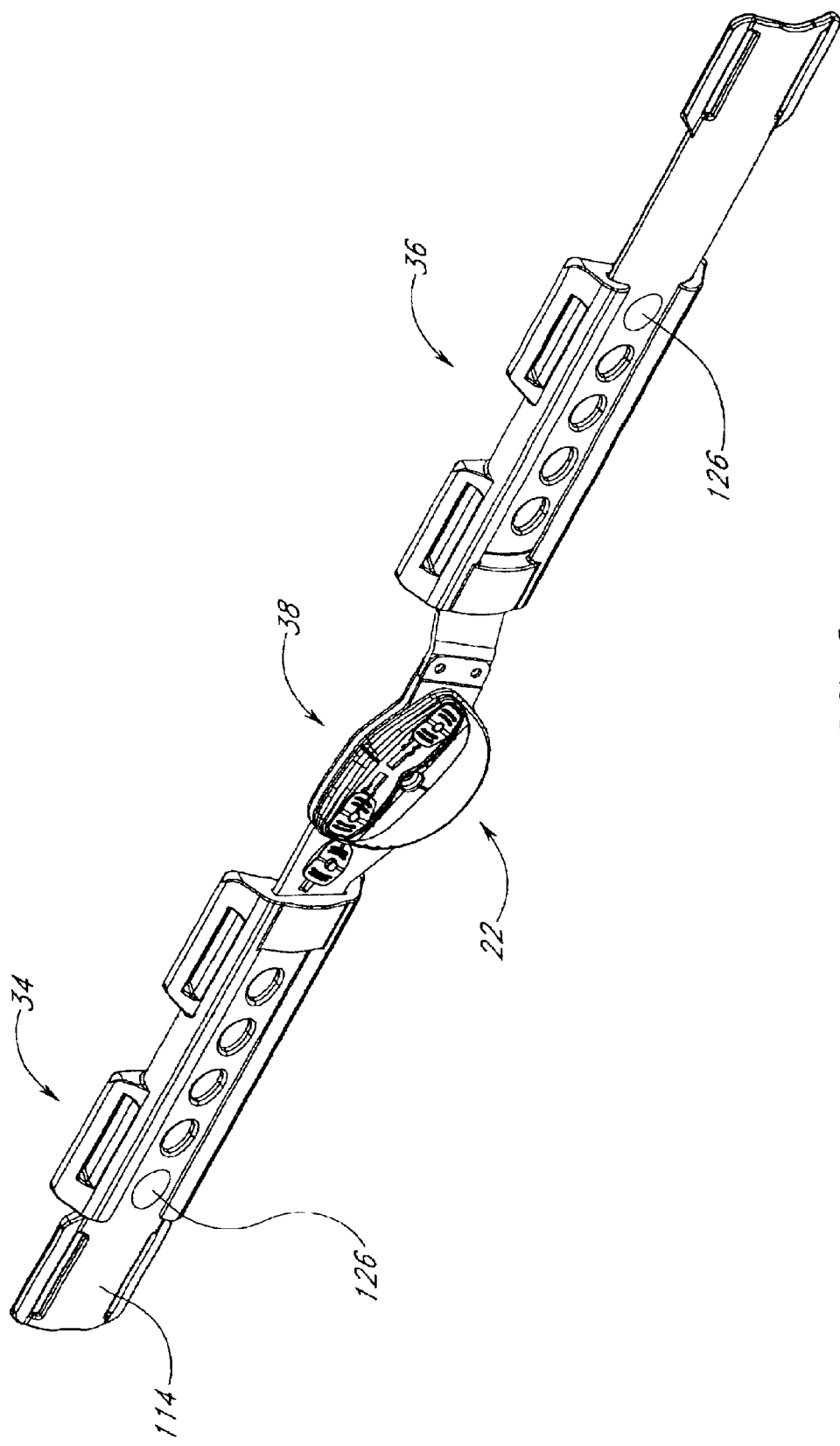
FIG. 3 is a perspective view of another preferred embodiment of the orthopedic brace including a right support.

FIG. 3 illustrates the right support 22 in detail. In the illustrated embodiment, the support 22 includes a thigh portion 34 and a calf portion 36. A hinge portion 38 rotatably connects the thigh portion 34 and calf portion 36. The hinge portion 38 may comprise any of a variety of well-known hinges. However, examples of preferred hinge types are described in U.S. Pat. Nos. 5,921,946 to Tillinghast, and 5,443,444 to Pruyssers, the entirety of which are incorporated herein by reference.

Figure 4:
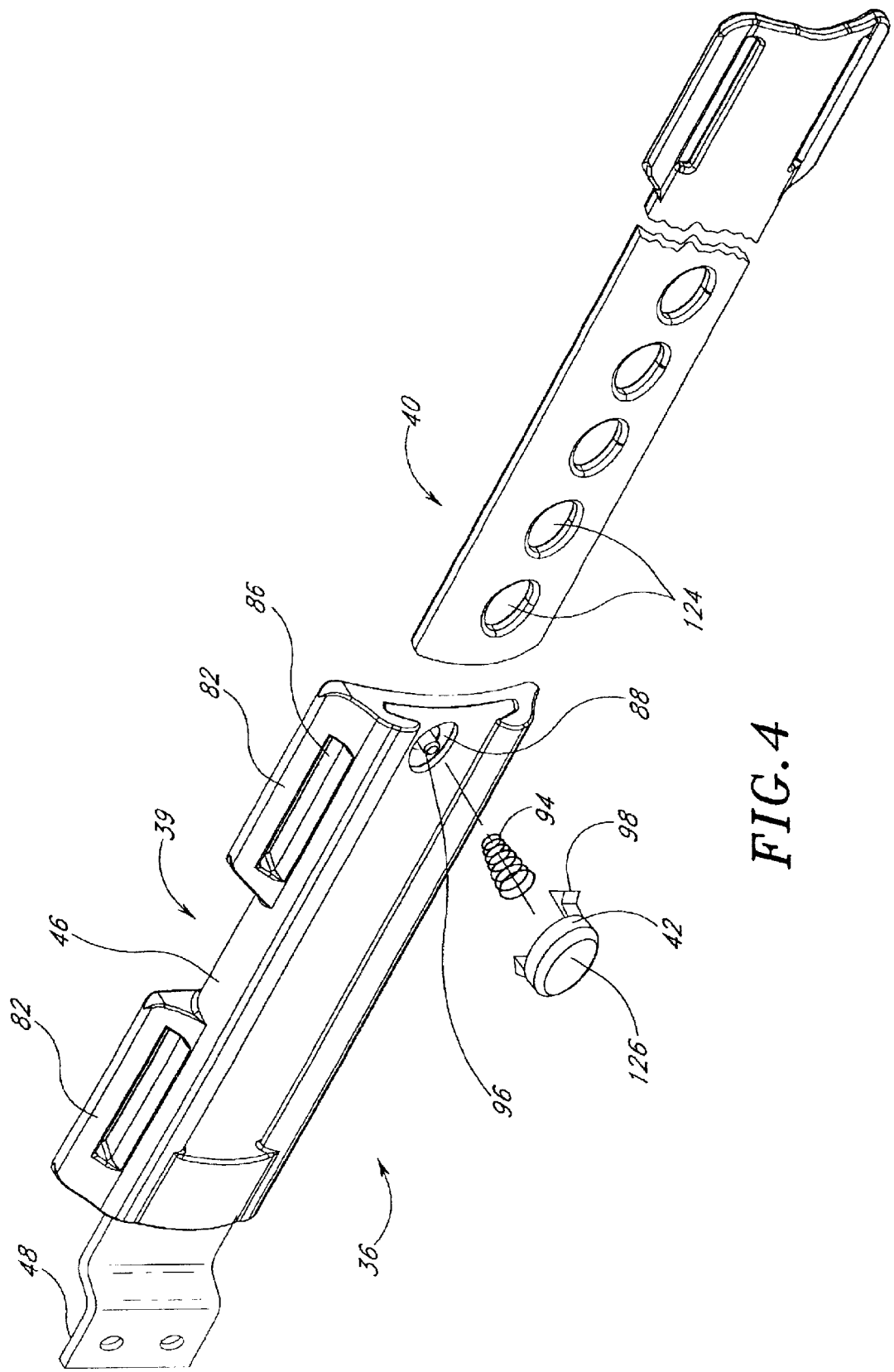
FIG. 4 is an exploded perspective view of a calf portion of the brace of FIG. 3.

FIG. 4 is an exploded perspective view of the calf portion 36 of the right support 22. The thigh portion 34 is substantially identical to the calf portion 36, with a few exceptions. The calf portion 36 preferably comprises a link bar 39, a sliding upright 40, and a button 42. When assembled, the button 42 nests inside the link bar 39, as described below.

The link bar 39 in turn is constructed of two pieces, as shown in FIGS. 5A–5E and 6A–6D. A first piece, or hinge plate 44, 48, is fixedly connected at a first end to a second piece, or channel member 46. Each of the thigh portion 34 and calf portion 36 includes an identical channel member 46. A second end of the hinge plate 44, 48 is rotatably connected to the hinge portion 38 (FIG. 3). In the embodiment shown, the shape of the hinge plate 44 comprising the thigh portion 34 differs from the shape of the hinge plate 48 comprising the calf portion 36. The shapes and functions of the hinge plates 44, 48 are described in detail in the above-referenced patent to Tillinghast.

FIGS. 7A–8B illustrate preferred embodiments of the hinge plates 44, 48. Each hinge plate 44, 48 includes a base portion 50 that is secured to the corresponding channel member 46, and an extended portion 52, 54 that is disposed adjacent the channel member 46. The base portion 50 may be embedded within the channel member 46, or may be secured to the channel member 46 in another appropriate fashion, such as with bolts or rivets. The base portion 50 of each hinge plate 44, 48 is a flat, substantially rectangular plate preferably having at least one through hole 56 and at least one notch 58 along a side 60 thereof.

Figure 8B:
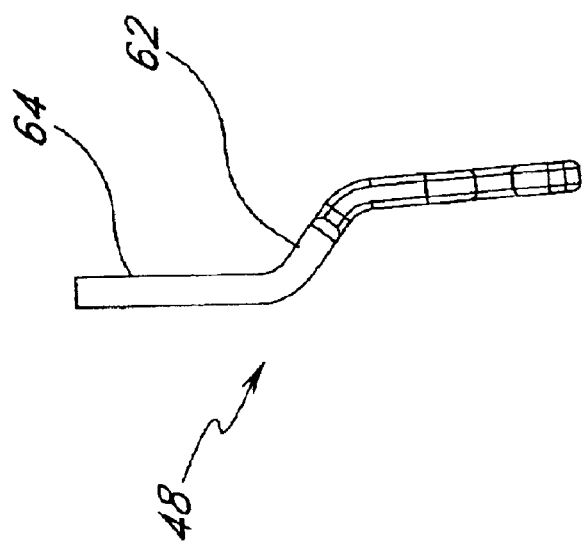
FIG. 8B is a right-side elevation view of the hinge plate of FIG. 8A.
Figure 8A:
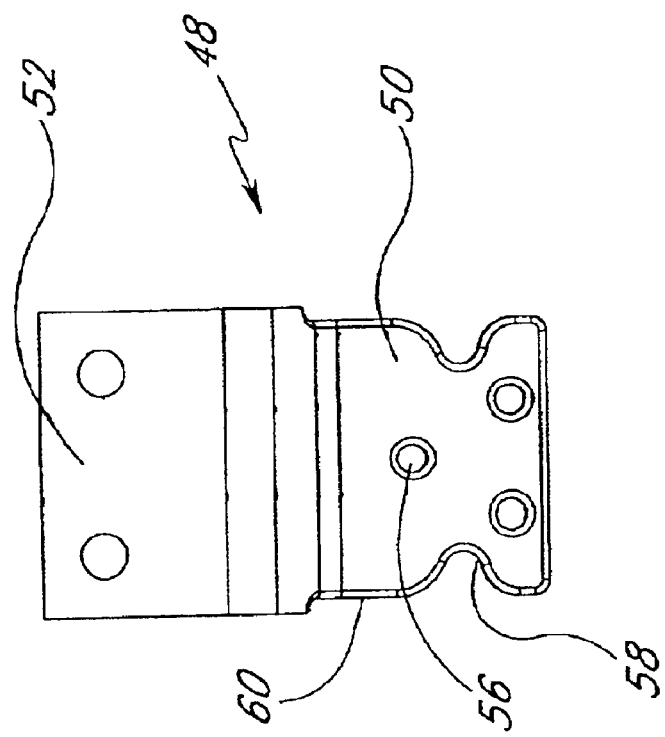
FIG. 8A is a top plan view of a hinge plate of the link bar of FIG. 6A.

Referring to FIG. 8B, the extended portion 52 of the calf hinge plate 48 includes a ramp portion 62 that extends at an angle from the base portion 50, and a second flat, substantially rectangular plate 64 that lies in a plane that is substantially parallel to that of the base portion 50. The extended portion 54 of the thigh hinge plate 44 (FIGS. 7A and 7B) comprises an oblong flat plate 66 extending at an angle from the base portion 50. The plate 66 preferably has a multi-contoured edge 68 that includes a plurality of cammed surfaces 70, extension limiting lands 72, and flexion limiting lands 74. The surface of the plate 66 includes a through bore 76 near an end of the plate 66 opposite the base portion 50, at least one elongate trough 78 extending substantially in the lengthwise direction of the plate 66, and a stepped slot 80 extending in substantially the same direction. The surface features of the hinge plates 44, 48 facilitate the operation of the hinge 38, which is described in detail in the above-referenced patent to Tillinghast.

The hinge plates 44, 48 are preferably constructed of aluminum or other pliable metal. Because of the wide variety of shapes and sizes of human legs, it is advantageous for a treating physician to be able to readily bend the knee brace 20 to more comfortably and effectively fit the contours of the leg. Aluminum and other pliable metals are relatively easy to bend by hand. These metals thus advantageously provide formability to the knee brace 20.

In the embodiment illustrated in FIGS. 5A–5E and 6A–6D, the channel member 46 is shaped as an elongate bar, having an integral, substantially D-shaped bracket 82 near each corner thereof. The brackets 82 project outwardly from the sides 84 of the channel member 46. Each bracket 82 defines a central slot 86 that is adapted to receive one of the straps 26. The straps 26 cooperate with the brackets to secure the brace 20 to the patient's leg.

Figure 4A:
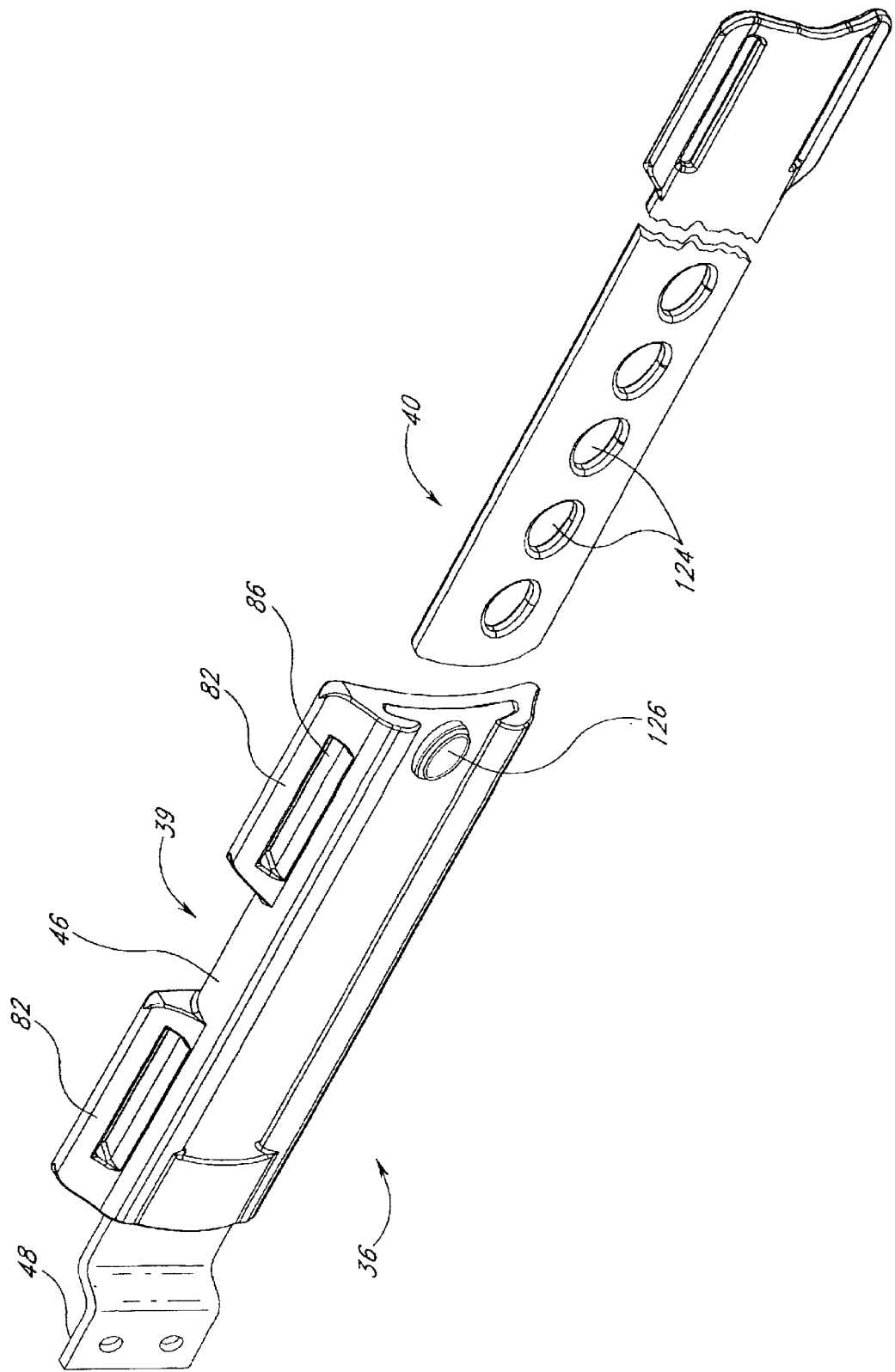
FIG. 4A is a partially exploded perspective view of the calf portion of FIG. 4.

A recess 88, elliptical in plan aspect, is provided in a floor 90 of each channel member 46 near an end 92 of the channel member 46 opposite the hinge plate 44, 48. The recess 88 houses the button 42 (FIG. 4), which is sized and shaped to fit within the interior of the recess 88. A spring 94 is disposed around a post 96 within the recess 88. A first end of the spring 94 abuts a lower surface of the button 42, and a second end of the spring 94 abuts a floor of the recess 88. The spring 94 thus biases the button 42 outwardly from the interior of the recess 88, such that an upper portion of the button 42 protrudes from the recess 88 (FIG. 4A). Retaining tabs 98 on the lower end of the button 42 extend through holes 100 (FIG. 5E) in the channel member 46 and prevent the button 42 from being completely expelled from the recess 88.

An inner surface 102 (FIGS. 5B and 6B) of the channel members 46 rests against the padded cuffs 28 when the brace 20 is worn. The inner surface 102 is preferably curved in cross-section to more closely fit the curved surface of the leg. The curvature helps to prevent the supports 22, 24 from shifting relative to the cuffs 28. An outer surface 103 (FIG. 5C and 6C) is also preferably curved in cross-section. The curved outer surface 103 gives the supports 22, 24 a more streamlined appearance, thereby reducing the risk that the supports 22, 24 will snag objects when the patient engages in physical activity. Those of skill in the art will appreciate that the supports 22, 24 need not include any curvature. Supports having substantially flat cross-sections do not depart from the spirit of the brace 20.

In a preferred embodiment, the inner surface 102 of the channel member 46 includes portions having different radii of curvature. The center portion 104 of the inner surface, as viewed from the side (FIGS. 5C and 6C), has a relatively short radius of curvature, while the outer portions 106 on either side of the center portion 104 each have a longer radius of curvature. The larger radius is selected to conform to the curved surface of the leg in order to increase patient comfort and provide a streamlined profile for the brace 20. The smaller radius of curvature of the center portion 104 increases the rigidity, or bending strength, of the channel member 46 without adding additional material. Additional material would tend to increase the weight of the channel member 46 and compromise its low profile. The small-radius center portion 104 also creates a gap between the center portion 104 of the inner surface 102 and the outer surface of the cuffs 28. This gap provides room for the inserts 32 and enables the button 42 to be depressed more easily while the brace 20 is worn. Without the gap, the retaining tabs 98 (FIG. 4) may interfere with the cuffs 28 when the button 42 is depressed.

Figure 5E:
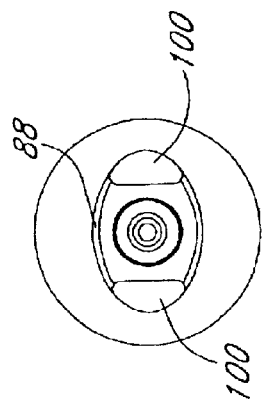
FIG. 5E is a detail view of a recess portion of the link bar of FIG. 5A.
Figure 5C:
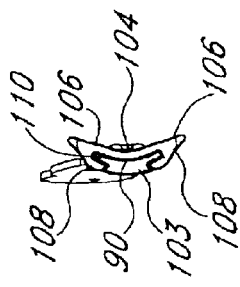
FIG. 5C is a right-side elevation view of the link bar of FIG. 5A.
Figure 5A:
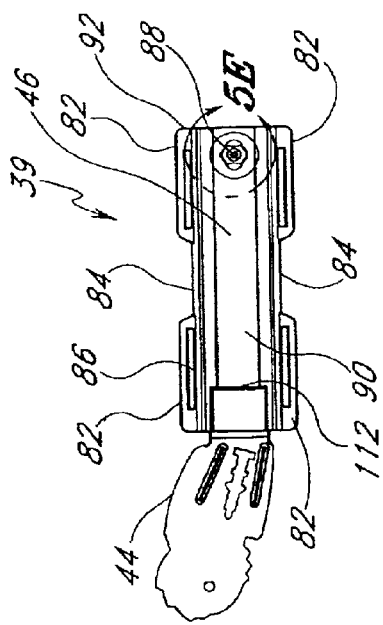
FIG. 5A is a top plan view of a link bar of a thigh portion the brace of FIG. 3.
Figure 5D:
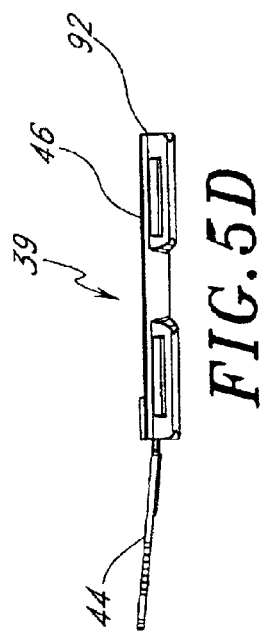
FIG. 5D is a front elevation view of the link bar of FIG. 5A.
Figure 5B:
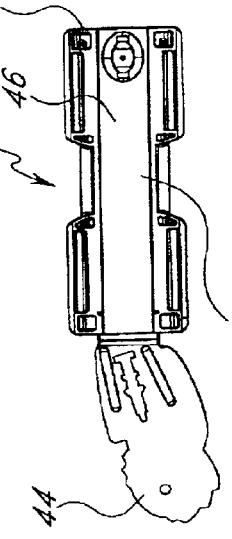
FIG. 5B is a bottom plan view of the link bar of FIG. 5A.
Figure 7B:
FIG. 7B is a right-side elevation view of the hinge plate of FIG. 7A.
Figure 7A:
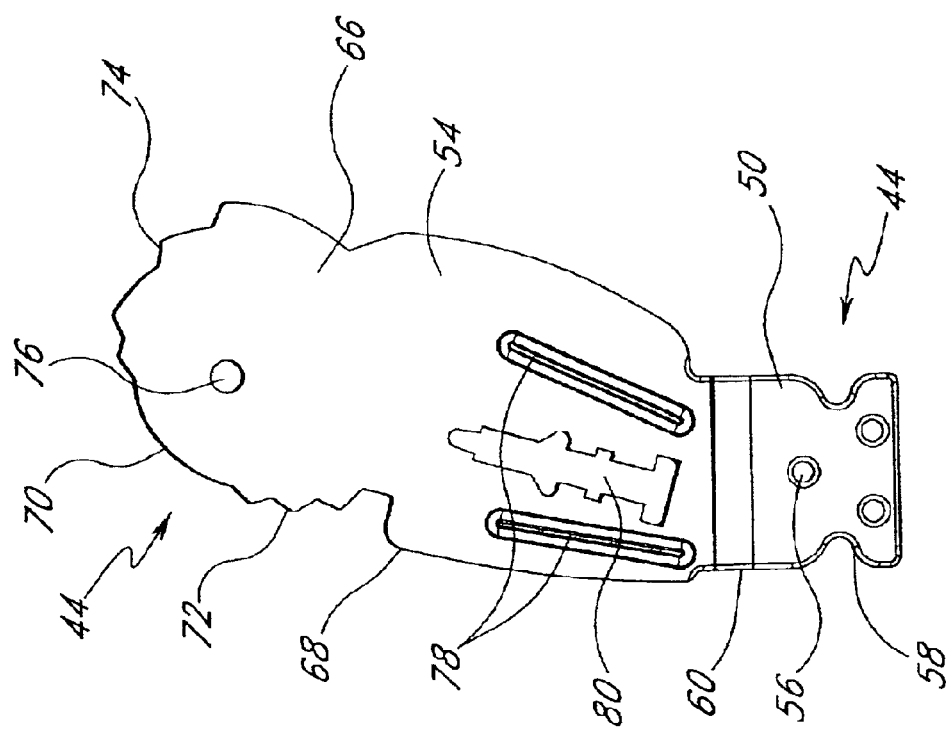
FIG. 7A is a top plan view of a hinge plate of the link bar of FIG. 5A.

The floor 90 of each channel member 46 is preferably similarly curved, and includes a pair of oppositely disposed flanges 108 at the sides thereof. The flanges 108 extend along most of the length of the channel member 46, creating a channel 110 that is substantially C-shaped in an end view (FIGS. 5C and 6C). The channel 110 has an open top. A first end 112 (FIGS. 5A and 5C) of the channel 110 near the hinge plate 44, 48 is closed, while a second end 92 of the channel 110 opposite the first end 112 is open.

The channel members 46 (FIGS. 5A and 6A) are preferably constructed of a composite material, and are formed by an insert molding process. A composite consisting of 83% thermoplastic nylon and 17% glass is a particularly preferred material for the channel members 46. During the insert molding process, the base portions 50 of the hinge plates 44, 48 are placed in an insert mold, after which a liquid composite is injected into the mold. The liquid composite surrounds the base portions 50, filling the holes 56 and notches 58. The composite that fills the holes 56 and notches 58 greatly strengthens the connection between the hinge plates 44, 48 and channel members 46 by increasing the pull-out strength of the hinge plates 44, 48. Rather than securing the hinge plates 44, 48 to the channel members 46 by an insert molding process, other conventional methods of attachment could be used. For example, screws or rivets may be used to secure the hinge plates 44, 48 to the channel members 46.

The combination of metal and composite in the supports 22, 24 imparts several advantages to the brace 20. First, insert molding is a relatively inexpensive process that enables complicated geometries to be formed with ease. Thus, even the complex shape of the channel members 46, which have contoured surfaces, ridges and tight interior corners, can be manufactured at relatively low cost. Surfaces and shapes such as these could not reasonably be formed from metal, at least not without undesirable additional cost. Second, the use of a bendable metal allows the brace 20 to be custom formed by a physician to fit the exact contours of the patient's leg. Thus, providing a link bar 39 (FIGS. 5A and 6A) that is formed from both metal and thermoplastic composite allows preferred embodiments of the brace 20 to include both of these advantages, rather than just one or the other.

A preferred embodiment of the sliding upright 40 is illustrated in detail in FIGS. 9A–9E. A second sliding upright 114, illustrated in detail in FIGS. 10A–10E, is substantially identical to the upright 40, except that the upright 40 includes an extension section 116 such that the upright 40 is longer than the upright 114. The difference in lengths between the upright 40 and upright 114 enables the brace 20 to better fit the patient's leg. Those of skill in the art will appreciate, however, that uprights of any suitable length, including uprights having equal lengths, are within the scope of the present orthopedic brace 20.

The uprights 40, 114 comprise an elongate bar with a pair of brackets 118 at one end thereof. The uprights 40, 114 nest within the channel members 46 of the calf portion 36 and thigh portion 34, respectively. The brackets 114 are similar in size, shape and orientation to the brackets 82 of the channel members 46, and are designed to receive the straps 26 within a central slot 120 for securing the brace 20 to the patient's leg. A center of an end 119 of each upright 40, 114 adjacent the brackets includes an indentation 121. The indentations 121 increase patient comfort by preventing interference between the sliding uprights 40, 114 and the patient's malleoli. Those of skill in the art will appreciate that the indentations are not necessary to achieve the objects of the orthopedic brace 20.

Each of the uprights 40, 114 has a curved cross-section (FIGS. 9D–9E and 10D–10E) of substantially the same radius as the floor 90 of the channel member 46. The curved contour not only allows the uprights 40, 114 to fit within the channels 110, but it also provides the uprights 40, 114 with greater rigidity. As with the channel members 46, discussed above, the uprights 40, 114 need not be curved in cross-section. Preferably, however, the uprights have appropriate cross-sectional shapes to fit within the channels in the channel members. The uprights 40, 114 may also be provided with a cross-section of variable thickness, if desired, to further increase the stiffness of the uprights 40, 114.

The thickness of the uprights 40, 114 near the edges 122 thereof allows the uprights 40, 114 to fit beneath the flanges 108 of the channel members 46. The uprights 40, 114 are thus configured to enter the open ends 92 of the channels 110 and slide longitudinally within the channels 110. The flanges 108 extend over the edges 122 of the uprights 40, 114 to prevent lateral separation of the uprights 40, 114 from the channel members 46. The slidability of the uprights 40, 114 within the channels 110 allows the length of the brace 20 to be adjusted.

Each of the uprights 40, 114 contains a plurality of spaced-apart elliptical holes 124 along a longitudinal axis thereof. The holes 124 desirably have substantially the same size, shape and orientation as the button 42. As the uprights 40, 114 slide within the channels 110, the holes 124 consecutively pass over the button 42. As each hole 124 passes, the biasing spring 94 forces the button 42 into the hole 124. The button 42 prevents further translation of the uprights 40, 114 through the channels 110, until an operator depresses the button 42 and holds it down while translating the uprights 40, 114 within the channels 110. The button 42 and corresponding holes 124 may be of any suitable shape.

The relatively large size and elliptical shape of the holes 110 and the button 42 allow the button 42 to be easily actuated by a finger or thumb of the operator. This configuration greatly reduces the difficulty of adjusting the brace 20, because the operator has one hand free to manipulate the uprights 40, 114 while holding down the button 42 with the finger or thumb.

When the button 42 is disposed within a hole 124, a top surface 126 (FIG. 4) of the button 42 is preferably flush with, or recessed below, the outer surface of the uprights 40, 114 as in FIG. 3. This arrangement reduces the risk that the button 42 will be accidentally activated if the wearer, for example, bumps into a table or chair.

The length adjustability of the brace 20, having push-button activation, provides the brace 20 with a number of advantages. First, the brace 20 is adapted to fit a wide variety of patients without the need for complicated adjustments. To fit the brace 20 to a patient, a physician individually adjusts the length of the thigh portion 34 and calf portion 36. The adjustment procedure for each portion 34, 36 is substantially identical, and the physician may adjust the portions 34, 36 in any order. To illustrate, however, adjustment of the thigh portion 34 will be described.

The physician depresses the button 42 by applying pressure to the button top surface 126 (FIG. 3) with his or her thumb or finger. When at least a leading edge of the button top surface 126 is below the hole 124, the upright 114 is freely translatable within the channel 110 (FIG. 5C) in either direction. Because the button 42 is biased outwardly by the spring 94 (FIG. 4), as the physician translates the upright 114 the button 42 will automatically pop into each successive hole 124 as each passes over the button 42, thereby locking the upright 114 in place with respect to the channel member 46. Each time the button 42 pops out, the physician pushes it back in and continues translating the upright 114 until the button 42 pops into the desired hole 124. When the button 42 pops into the desired hole 124, the upright 114 is securely locked with respect to the channel member 46.

Second, since preferred embodiments of one brace 20 will fit many patients of different sizes, hospitals need not maintain a large inventory of differently sized braces. With some prior art braces, length adjustment effectively means substituting a brace of one size with a differently sized brace. Thus, hospitals must maintain a large inventory of braces of all different sizes in order to accommodate the wide variety of patients that they regularly treat. With preferred embodiments of the brace 20, hospitals need only keep a supply of one brace 20. Physicians then adjust the length of the brace 20 as needed to fit individual patients.

Figure 11:
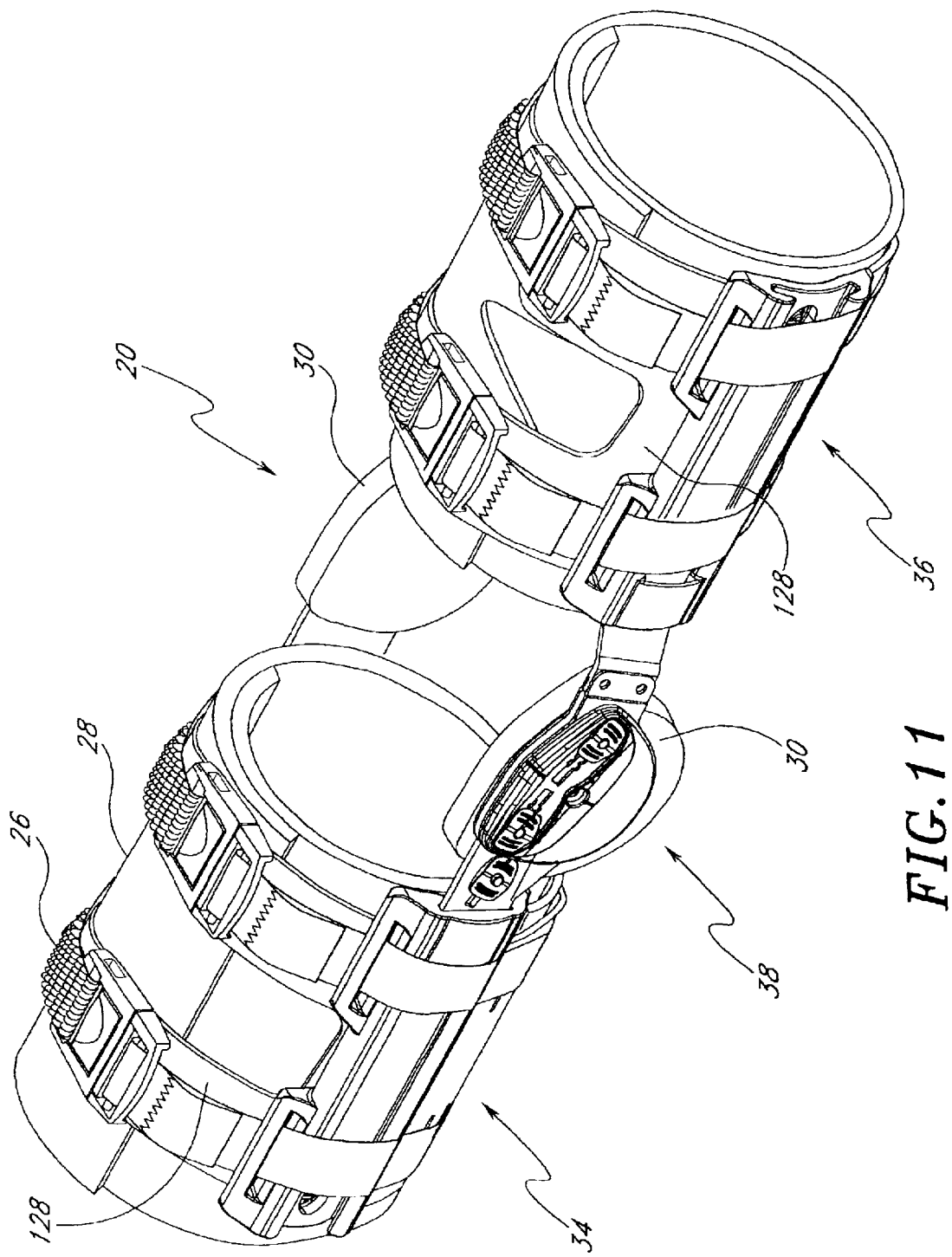
FIG. 11 is a perspective view of a preferred embodiment of the orthopedic brace including a right support and a left support, padded cuffs and straps, wherein sliding uprights of each support have been removed.
Figure 12:
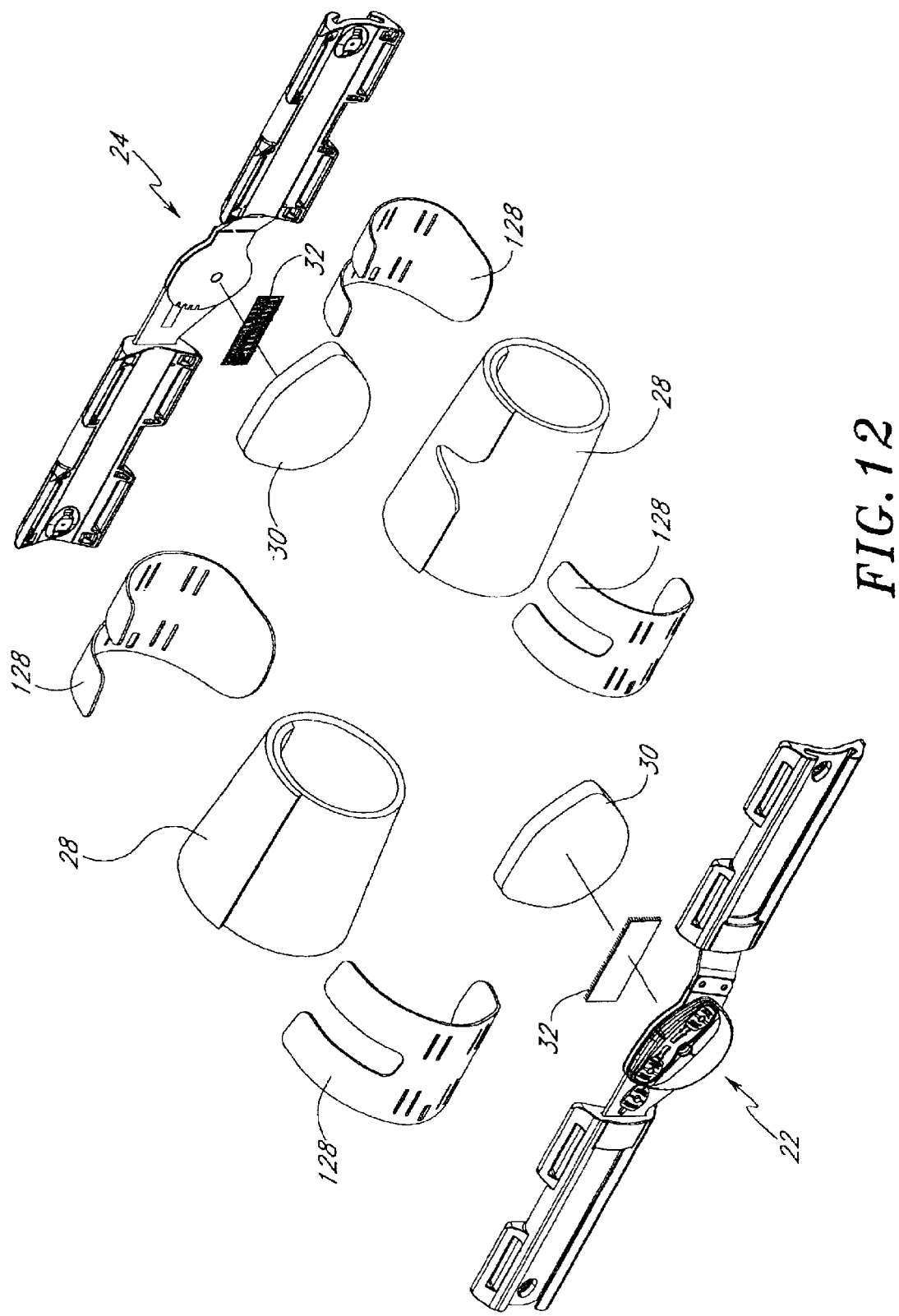
FIG. 12 is a partially exploded perspective view of the brace and padded cuffs of FIG. 11.

Third, as the patient progresses through therapy, it is often desirable to reduce the amount of support provided by the brace 20, such as by shortening the length of the brace 20. With preferred embodiments of the brace 20, however, the uprights 40, 114 may be retracted to decrease the overall length of the brace 20. Alternatively, if an even shorter brace 20 is desired, one or both uprights 40, 114 may be completely removed from their respective channels 110. The remaining length of the supports 22, 24, which consists of the link bars 39 and the hinge portion 38, may then be used in isolation, as shown in FIGS. 11 and 12. Removal of the uprights 40, 114 is quick and easy, requiring only that the button 42 be depressed while the uprights 40, 114 are drawn completely out of the channels 110. The brace 20 is thus far more versatile than prior art designs.

The embodiment of the brace 20 depicted in FIGS. 11 and 12 includes shells 128 disposed between the supports 22, 24 and the cuffs 28. The shells 128 comprise semi-rigid members that aid in providing even compression about the patient's leg. Preferably the shells 128 are constructed of a plastic. However, any semi-rigid material could be used.

In the pictured embodiment, each shell 128 is shaped substantially as a half-cylinder. Thus, two shells 128 comprise a thigh-encircling portion, and two shells 128 comprise a calf-encircling portion. Those of skill in the art will appreciate that the shells 128 may be constructed in a variety of alternative ways. For example, the thigh-or calf-encircling portion could be shaped as a complete cylinder with a longitudinal split so that the cylinder may be wrapped around the patient's leg. Those of skill in the art will also appreciate that the shells 128 may be used with the embodiment of the brace 20 depicted in FIGS. 1 and 2. Finally, those of skill in the art will also appreciate that the shells 128 are not necessary to achieve the objects of the orthopedic brace 20.

SCOPE OF THE INVENTION

The above presents a description of the best mode contemplated for the present orthopedic brace having length-adjustable supports, and of the manner and process of making and using it, in such full, clear, concise and exact terms as to enable any person skilled in the art to which it pertains to make and use this brace. This brace is, however, susceptible to modifications and alternate constructions from that discussed above which are fully equivalent. Consequently, it is not the intention to limit this brace to the particular embodiments disclosed. On the contrary, the intention is to cover all modifications and alternate constructions coming within the spirit and scope of the brace as generally expressed by the following claims, which particularly point out and distinctly claim the subject matter of the brace.

What is claimed is:

1. An orthopedic brace, comprising:

a first support;

a second support; and a hinge assembly rotatably connecting the first and second supports, wherein at least one of the first and second supports comprises a first portion constructed of a thermoplastic composite and a second portion constructed of a metal;

the first portion is connected to a metal hinge plate; and the hinge plate is insert molded within the first portion.

2. An orthopedic brace, comprising:

a first support;

a second support; and a hinge assembly rotatably connecting the first and second supports, wherein at least one of the first and second supports comprises an outer portion defining a longitudinal channel and a telescoping upright movable in the channel to adjust a length of the support; and a plurality of engagement surfaces are provided along a length of the telescoping upright, and the outer portion includes an engagement member selectively engageable with at least one of the engagement surfaces to lock the telescoping portion in place in the channel.

3. The orthopedic brace of claim 2, wherein the engagement member is recessed within the upright when the engagement member engages the at least one of the engagement surfaces.

4. The orthopedic brace of claim 3, wherein the engagement member comprises a button disposed within a recess in the channel and biased toward a configuration wherein a portion of the button protrudes from a surface of the channel.

5. The orthopedic brace of claim 4, wherein the button has an oval shape in plan aspect.

6. The orthopedic brace of claim 2, wherein the engagement surfaces comprise holes.

7. The orthopedic brace of claim 6, wherein the holes have an oval shape in plan aspect.

8. An orthopedic brace, comprising:

a first support;

a second support; and a hinge assembly rotatably connecting the first and second supports, wherein at least one of the first and second supports comprises an outer portion defining a longitudinal channel and a telescoping upright movable in the channel to adjust a length of the support;

the first and second supports are curved about an axis that is parallel to a longitudinal axis of the brace; and a cross-section of the first and second supports includes a first region having a first radius of curvature and a second region having a second radius of curvature longer than the first radius of curvature.

9. The orthopedic brace of claim 8, wherein the first region is located between the second region and a third region having the second radius of curvature.

10. An orthopedic brace, comprising:

a first support;

a second support; and a hinge assembly rotatably connecting the first and second supports, wherein at least one of the first and second supports comprises an outer portion defining a longitudinal channel and a telescoping upright movable in the channel to adjust a length of the support; and the first and second supports further comprise at least a first generally D-shaped ring on a first side and a second generally D-shaped ring on a second side opposite the first side.

11. The orthopedic brace of claim 10, wherein the first and second rings are adjacent the hinge assembly.

12. An orthopedic brace, comprising:

a first support;

a second support; and a hinge assembly rotatably connecting the first and second supports, wherein at least one of the first and second supports comprises an outer portion defining a longitudinal channel and a telescoping upright movable in the channel to adjust a length of the support; and the upright comprises at least a first generally D-shaped ring on a first side and a second generally D-shaped ring on a second side opposite the first side.

13. The orthopedic brace of claim 12, wherein the first and second rings are located at an end of the upright opposite the hinge assembly.

14. An orthopedic brace, comprising:

a first length-adjustable support including a longitudinal channel and a sliding upright slidably engaging the channel;

a second length-adjustable support including a longitudinal channel and a sliding upright slidably engaging the channel; and a hinge assembly rotatably connecting the first and second supports, wherein each sliding upright includes a plurality of through holes, and a floor of each channel includes a spring-biased button engageable with each hole such that the button positively locks a position of the upright with respect to the channel and the upright is slidable within the channel when the button is depressed.

15. The orthopedic brace of claim 14, wherein each support includes a curvature about a longitudinal axis thereof such that substantially all of a surface of each support that faces a patient's leg contacts the leg.

16. The orthopedic brace of claim 14, wherein each support further comprises a plurality of brackets that are adapted to receive flexible straps for securing the brace to a patient's leg.

* * * * *